(12) United States Patent
Bossi et al.

(10) Patent No.: US 7,757,558 B2
(45) Date of Patent: Jul. 20, 2010

(54) METHOD AND APPARATUS FOR INSPECTING A WORKPIECE WITH ANGULARLY OFFSET ULTRASONIC SIGNALS

(75) Inventors: Richard H. Bossi, Renton, WA (US); Robert L. Carlsen, Kent, WA (US); Gary E. Georgeson, Federal Way, WA (US)

(73) Assignee: The Boeing Company, Chicago, IL (US)

( * ) Notice: Subject to any disclaimer, the term of this patent is extended or adjusted under 35 U.S.C. 154(b) by 464 days.

(21) Appl. No.: 11/687,950

(22) Filed: Mar. 19, 2007

(65) Prior Publication Data

US 2008/0229834 A1      Sep. 25, 2008

(51) Int. Cl.
*G01N 9/24* (2006.01)
(52) U.S. Cl. .......................... 73/609; 73/628
(58) Field of Classification Search ............ 73/609, 73/614, 620, 627, 628, 629
See application file for complete search history.

(56) References Cited

U.S. PATENT DOCUMENTS

| | | | |
|---|---|---|---|
| 3,712,119 A * | 1/1973 | Cross et al. ................ | 73/614 |
| 4,058,003 A | 11/1977 | Macovski | |
| 4,487,070 A | 12/1984 | Gerling et al. | |
| 4,591,511 A | 5/1986 | Peebles, Jr. | |
| 4,596,145 A | 6/1986 | Smith et al. | |
| 4,869,109 A | 9/1989 | Miglianico et al. | |
| 4,881,177 A | 11/1989 | McClean et al. | |
| 5,005,420 A | 4/1991 | Miyajima | |
| 5,073,814 A | 12/1991 | Cole, Jr. et al. | |
| 5,091,893 A | 2/1992 | Smith et al. | |
| 5,165,270 A | 11/1992 | Sansalone et al. | |
| 5,390,544 A * | 2/1995 | Madras ................. | 73/602 |
| 5,614,670 A | 3/1997 | Nazarian et al. | |
| 5,680,863 A | 10/1997 | Hossack et al. | |
| 5,735,282 A | 4/1998 | Hossack | |
| 5,814,731 A | 9/1998 | Alexander et al. | |

(Continued)

FOREIGN PATENT DOCUMENTS

GB      1474932 A      5/1977

OTHER PUBLICATIONS

Manohar Bashyam, *Ultrasonic NDE for Ceramic—And Metal—Matrix Composite Material Characterization*, Review of Progress in Quantitative Nondestructive Evaluation, 1991, pp. 1423-1430, vol. 10B, Plenum Press, New York, NY.

(Continued)

*Primary Examiner*—John E Chapman
(74) *Attorney, Agent, or Firm*—Alston & Bird LLP

(57) ABSTRACT

A method and apparatus are provided to identify unacceptable levels of porosity, microcracking or defects attributable to thermal damage. Ultrasonic signals are introduced into the workpiece, such as by means of an ultrasonic transmitter. The ultrasonic signals propagate along a predefined axis of propagation oriented at an offset angle relative to a predefined reference direction oriented normal to the workpiece. Backscattered signals are received, such as by an ultrasonic receiver, from the workpiece. A measure representative of the cumulative energy of the backscattered signals received over a predefined time interval is then determined, such as integration performed by a processing element. An anomalous response may then be detected based upon the measure representative of the cumulative energy of the backscattered signals. This anomalous response may be representative of at least a predefined amount of porosity, microcracking or thermal damage.

18 Claims, 5 Drawing Sheets

U.S. PATENT DOCUMENTS

| | | | |
|---|---|---|---|
| 5,983,701 | A | 11/1999 | Hassani et al. |
| 6,234,025 | B1 | 5/2001 | Gieske et al. |
| 6,424,597 | B1 | 7/2002 | Bolomey et al. |
| 6,446,509 | B1 | 9/2002 | Takada et al. |
| 6,476,541 | B1 | 11/2002 | Smith et al. |
| 6,586,702 | B2 | 7/2003 | Wiener-Avnear et al. |
| 6,591,679 | B2 | 7/2003 | Kenefick et al. |
| 6,598,485 | B1 | 7/2003 | Lin et al. |
| 6,656,124 | B2 | 12/2003 | Flesch et al. |
| 6,681,466 | B2 | 1/2004 | David et al. |
| 6,691,576 | B1 | 2/2004 | Sato et al. |
| 6,777,931 | B1 | 8/2004 | Takada et al. |
| 6,798,717 | B2 | 9/2004 | Wiener-Avnear et al. |
| 6,822,374 | B1 | 11/2004 | Smith et al. |
| 2002/0128790 | A1 | 9/2002 | Woodmansee |
| 2004/0123665 | A1 | 7/2004 | Blodgett et al. |
| 2005/0132809 | A1 | 6/2005 | Fleming et al. |
| 2006/0004499 | A1 | 1/2006 | Trego et al. |
| 2006/0186260 | A1 | 8/2006 | Magnuson et al. |
| 2007/0051177 | A1 | 3/2007 | Gifford et al. |

OTHER PUBLICATIONS

S.M. Handley, M.S. Hughes, J.G. Miller, E.I. Madaras, *Characterization of Porosity in Graphite/Epoxy Composite Laminates With Polar Backscatter and Frequency Dependent Attenuation*, Ultrasonics Symposium, 1987, pp. 827-830, 0090-5607/87/0000-0827 IEEE.

Daniel Grolemund, Chen S. Tsai, *Statistical Moments of Backscattered Ultrasound in Porous Fiber Reinforced Composites*, IEEE Transactions on Ultrasonics, Ferroelectrics, and Frequency Control, Mar. 1998, pp. 295-304, vol. 45, No. 2.

Lewis T. Thomas III, Eric I. Madaras, J.G. Miller, *Two-Dimensional Imaging of Selected Ply Orientations In Quasi-Isotropic Composite Laminates Using Polar Backscattering*, Ultrasonics Symposium, 1982, pp. 965-970, 0090-5607/82/0000-0965 IEEE.

F. Aymerich, S. Meili, *Ultrasonic Evaluation of Matrix Damage in Impacted Composite Laminates*, Composites Part B: Engineering, Jan. 2000, pp. 1-6, vol. 31, Issue 1, S359-8368(99) 00067-0.

Atul S. Ganpatye, *Ultrasonic Ply-by-ply Detection of Matrix Cracks in Laminated Composites*, 43$^{rd}$ AIAA Aerospace Sciences Meeting and Exhibit, American Institute of Aeronautics and Astronautics, Inc., Jan. 2005, pp. 1-9. Reno, Nevada.

Y. Bar-Cohen, R.L. Crane, *Acoustic-Backscattering Imaging of Subcritical Flaws in Composites*, Materials Evaluation 40, 1982, pp. 970-975 (6 pages).

J. Qu, J.D. Achenbach, *Analytical Treatment of Polar Backscattering From Porous Composites*, Review of Progress in Quantitative Nondestructive Evaluation, 1987, pp. 1137-1146, vol. 6B, Plenum Press, New York, NY.

J. Qu, J.D. Achenbach, *Backscatter From Porosity in Cross-Ply Composites*, Review of Progress in Quantitative Nondestructive Evaluation, 1988, pp. 1029-1036, vol. 7B, Plenum Press, New York, NY.

Ronald A. Roberts, *Characterization of Porosity in Continuous Fiber-Reinforced Composites With Ultrasonic Backscatter*, Review of Progress in Quantitative Nondestructive Evaluation, 1988, pp. 1053-1062, vol. 7B, Plenum Press, New York, NY.

T. Ohyoshi, J.D. Achenback, *Effect of Bottom-Surface Reflections on Backscatter From Porosity in a Composite Layer*, Review of Progress in Quantitative Nondestructive Evaluation, 1988, pp. 1045-1052, vol. 7B, Plenum Press, New York, NY.

Ronald A. Roberts, *Porosity Characterization in Fiber-Reinforced Composites by Use of Ultrasonic Backscatter*, Review of Progress in Quantitative Nondestructive Evaluation, 1987, pp. 1147-1156, vol. 6B, Plenum Press, New York, NY.

International Search Report for PCT Application No. PCT/2008/057165 filed Mar. 14, 2008; Date of Completion: May 28, 2008; Date of Mailing: Jun. 4, 2008.

Written Opinion for PCT Application No. PCT/2008/057165 filed Mar. 14, 2008; Date of Completion: May 28, 2008; Date of Mailing: Jun. 4, 2008.

Jocelyn Langlois and R.S. Frankle, *Use of Flexible Ultrasonic Arrays in Inspection*, NDT.NET—Mar. 1999, vol. 4, No. 3, 5 pages.

*General Provisions for Boeing (Buyer) Purchase Contract to Seller (Seller) for Flexible Ultrasonic Array Demonstration Unit*, privately exchanged between Buyer and Seller on approximately Mar. 24, 2004, never published, redacted copy 6 pages.

*SonoFlex™ Flexible Ultrasonic Array Systems*, The Boeing Company, Seattle, WA, publicly available at the Aging Aircraft Conference in Atlanta, Mar. 7-9, 2006, 1 page.

*Flexible Ultrasonic Arrays*, HD Laboratories, Inc., NDT and Electronic Engineers; 2 pages, available at http://www.hdlabs.com/NDT/FlexibleArrays/flexiblearrays.htm; Apr. 28, 2006; publicly available on or before Sep. 1, 2005; 2 pages.

* cited by examiner

METHOD AND APPARATUS FOR INSPECTING A WORKPIECE WITH ANGULARLY OFFSET ULTRASONIC SIGNALS

FIELD OF THE INVENTION

Embodiments of the present invention relate generally to an apparatus and method for inspecting a structure and, more particularly, to an apparatus and method for detecting porosity, microcracks or thermal damage via single-sided ultrasonic inspection of a structure.

BACKGROUND OF THE INVENTION

Non-destructive inspection (NDI) of structures involves thoroughly examining a structure without harming the structure or requiring its significant disassembly. Non-destructive inspection is typically preferred to avoid the schedule, labor, and costs associated with removal of a part for inspection, as well as avoidance of the potential for damaging the structure. Non-destructive inspection is advantageous for many applications in which a thorough inspection of the exterior and/or interior of a structure is required. For example, non-destructive inspection is commonly used in the aircraft industry to inspect aircraft structures for any type of internal or external damage to or defects (flaws) in the structure. Inspection may be performed during manufacturing or after the completed structure has been put into service, including field testing, to validate the continued integrity and fitness of the structure.

During NDI, one or more sensors may move over the portion of the structure to be examined, and receive data regarding the structure. Various types of sensors may be used to perform non-destructive inspection. For example, a pulse-echo (PE), through transmission (TT), or shear wave sensor may be used to obtain ultrasonic data, such as for thickness gauging, detection of laminar defects and porosity, and/or crack detection in the structure.

In some circumstances, only a single surface of the structure may be accessible for inspection purposes, thereby limiting the potential inspection techniques. For example, in the field, access to interior surfaces of the structure is often restricted, requiring disassembly of the structure and introducing additional time and labor. Similarly, during manufacture, one of the surfaces may be disposed upon a mandrel and be inaccessible, at least without undesirable and time-consuming disassembly.

While single-sided inspection techniques, such as PE, can be employed to detect disbonds, delaminations, cracks or other substantial defects, it may be difficult to detect porosity in certain situations, such as situations in which the structure under inspection is ultrasonically coupled to another structure, such as a mandrel or other backing material, absent a TT inspection technique. In this regard, in PE, the amplitude of the reflection from the back surface, i.e., the surface opposite the inspection sensor, is used as a gage to determine the percent of porosity by comparing the reflection from the back surface of the structure under inspection with standard data gathered from prior inspections of reference samples of known porosity. Accordingly, porosity may be difficult to detect and/or quantify, especially in conjunction with structures that are only amenable of single-sided inspection and are ultrasonically coupled to another structure, since the ultrasonic coupling will reduce the reflection from the back surface by an unknown amount. Such difficulties in accurately detecting and/or quantifying porosity may be problematic in composite manufacturing processes in which it is desirable to monitor the quality of the composite material including, for example, the porosity of the composite material to insure that the manufacturing process is performing in the desired manner.

While it is generally desirable to detect porosity during or following manufacture, it is similarly desirable to be able to identify microcracking or thermal damage in the field or otherwise once the composite material has been placed in service. Microcracking can occur due to fatique or thermal cycling of composites. Microcracks generally consist of multiple small cracks in the resin and fibers of a composite structure. Typical crack sizes are in the 0.010 inch to over 0.200 inch range. Thermal damage may be attributable to various sources and, in aerospace applications, may be attributable to engine exhaust impingement, overheated components in a wheel well or other confined space, or fires involving an auxiliary power duct or other component. Regardless of its source, thermal damage degrades the matrix properties and the interface between matrix material and the embedded fibers, thereby decreasing the structural properties of the composite material and oftentimes requiring repair or at least more frequent monitoring.

Conventionally, laboratory-based methods have been employed to detect and determine the extent of thermal damage. Unfortunately, the laboratory-based methods cannot generally be performed in the field and oftentimes require disassembly or other rework of the composite structure. As such, non-destructive methods of detecting thermal damage have been developed, including infrared (IR) spectroscopy, laser pumped florescence and high frequency eddy current inspection. However, IR spectroscopy and laser pumped fluorescence are generally localized techniques capable of measuring thermal damage within one to three plies of the surface. For thicker structures, plies must generally be successively removed and then the remaining structure re-inspected to detect thermal damage deeper within a structure, thereby increasing the time and cost required for an inspection. High frequency eddy current inspection measures the change in resistance in the matrix material, such as that change in resistance attributable to overheating. However, high frequency eddy current inspection is also a near surface inspection method and generally cannot be utilized if the composite structure includes lightening strike protection. High frequency eddy current inspection is also disadvantageously sensitive to conductive structures in the immediate vicinity of the inspection area and to the geometry of the structure.

Ultrasonic PE has also been employed in an effort to detect thermal damage. However, it may be difficult to detect thermal damage until the thermal damage is sufficiently substantial so as to result in discrete delaminations. Accordingly, thermal damage may be difficult to detect and/or quantify via ultrasonic PE at earlier stages of degradation.

In some instances, the thermal damage is not visible and conventional nondestructive inspection techniques do not detect the thermal damage, particularly in instances in which the composite material must be inspected from a single side for at least the reasons described above in conjunction with porosity detection. Moreover, even in instances in which it is suspected that a composite structure has suffered thermal damage, such as a result of surface charring or discoloring, a portion of the composite structure may be removed and replaced. However, the removal and replacement may later prove to be completely unnecessary in instances in which the composite structure has, in fact, not been thermally damaged. Alternatively, the removal and replacement may later prove to be excessive in instances in which a larger portion of the composite structure is removed and replaced out of precaution than has been actually thermally damaged.

BRIEF SUMMARY OF THE INVENTION

A method and apparatus for inspecting a workpiece are therefore provided that have embodiments that address at least some of the deficiencies identified with conventional techniques. In this regard, the method and apparatus of embodiments of the present invention can identify unacceptable levels of porosity, microcracking or defects attributable to thermal damage, even in instances in which the workpiece can only be inspected from a single side. As such, the method and apparatus of embodiments of the present invention are suitable for inspection either during manufacturing or once a workpiece has been placed in service in the field.

According to one embodiment, ultrasonic signals are introduced into the workpiece, such as by means of an ultrasonic transmitter. The ultrasonic signals propagate along a predefined axis of propagation oriented at an offset angle, such as between about 5° and 45°, relative to a predefined reference direction oriented normal to the workpiece. In one embodiment, for example, a shoe defines the offset angle and carries at least a portion of the ultrasonic transmitter, such as one or more ultrasonic transducers. Backscattered signals are received, such as by an ultrasonic receiver, in response to the ultrasonic signals introduced into the workpiece. In one embodiment, the ultrasonic signals are alternately introduced into and received from the workpiece at each of a plurality of locations across the workpiece in order to thoroughly inspect at least a portion of the workpiece.

A measure representative of the cumulative energy of the backscattered signals received over a predefined time interval is then determined, such as by a processing element. In one embodiment, the measure representative of the cumulative energy of the backscattered signals is determined by integrating the energy of the backscattered signals received over the predefined time interval. An anomalous response from the workpiece may then be detected based upon the measure representative of the cumulative energy of the backscattered signals. This anomalous response may be representative of at least a predefined amount of porosity or microcracking within a workpiece or thermal damage to the workpiece.

In addition to the method and apparatus for inspecting a workpiece as described above, a control apparatus is also provided according to another aspect of the present invention. The control apparatus includes a processing element configured to direct the ultrasonic transmitter and the ultrasonic receiver, as well as to process the received signals in order to determine a measure representative of the cumulative energy of the backscattered signals over a predefined time interval and to detect an anomalous response from the workpiece based thereupon.

By determining and then analyzing the cumulative energy of the backscattered signals over a predefined time period, the aggregate effect of porosity, microcracking and/or thermal damage at a particular location can be more accurately assessed and anomalies can be detected even in instances in which the contribution from a single pore, a single microcrack or a single defect attributable to thermal damage would not otherwise be identified as anomalous. By utilizing backscattered signals and, accordingly, permitting inspection from a single side of the workpiece, the method and apparatus of embodiments of the present invention do not require disassembly of the workpiece and, instead, permit inspection while the workpiece remains upon a mandrel or other tooling, such as during manufacture, or remains in an assembled form, such as while in the field or otherwise in service.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

Figure 4A:
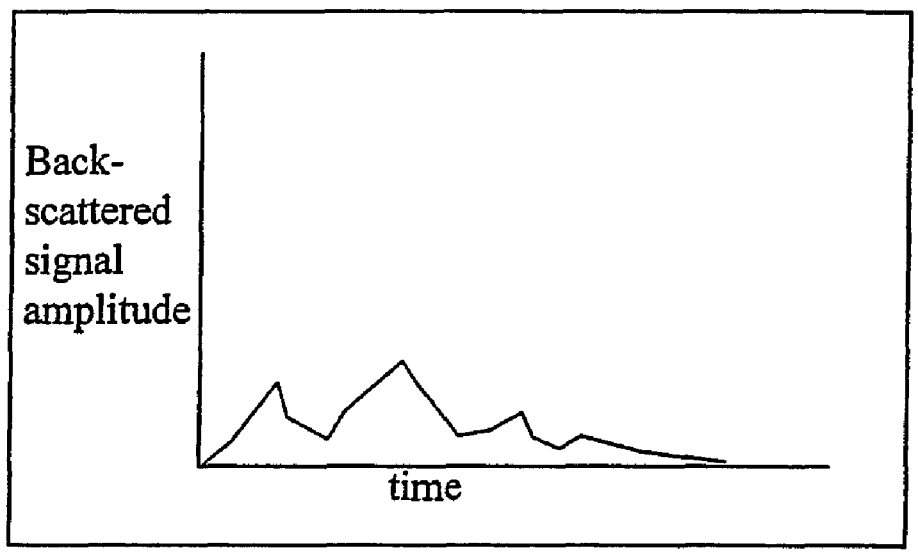
Figure 4B:
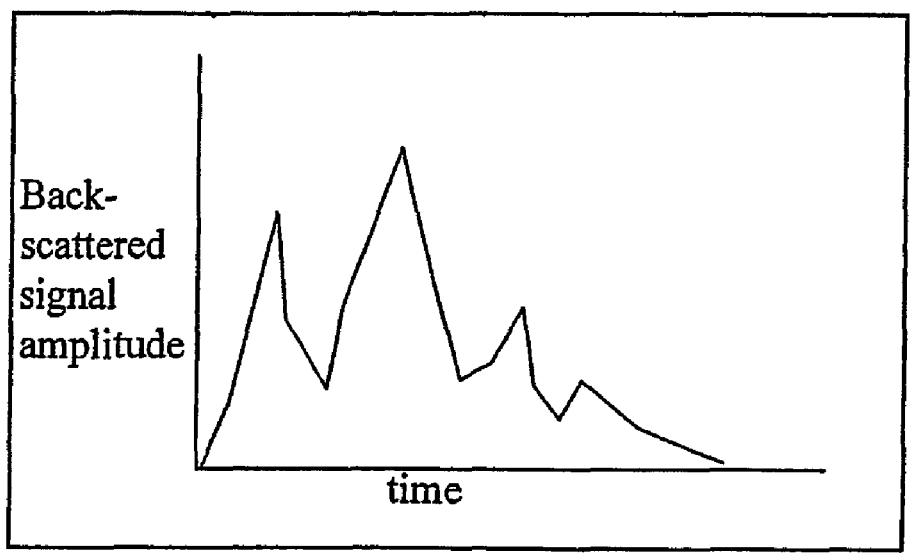
Figure 5:
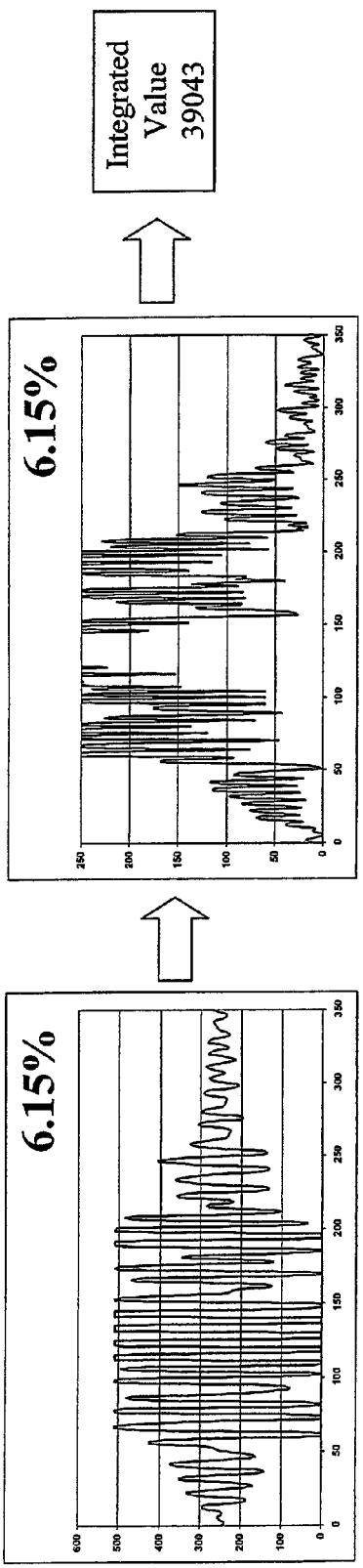
Figure 6:
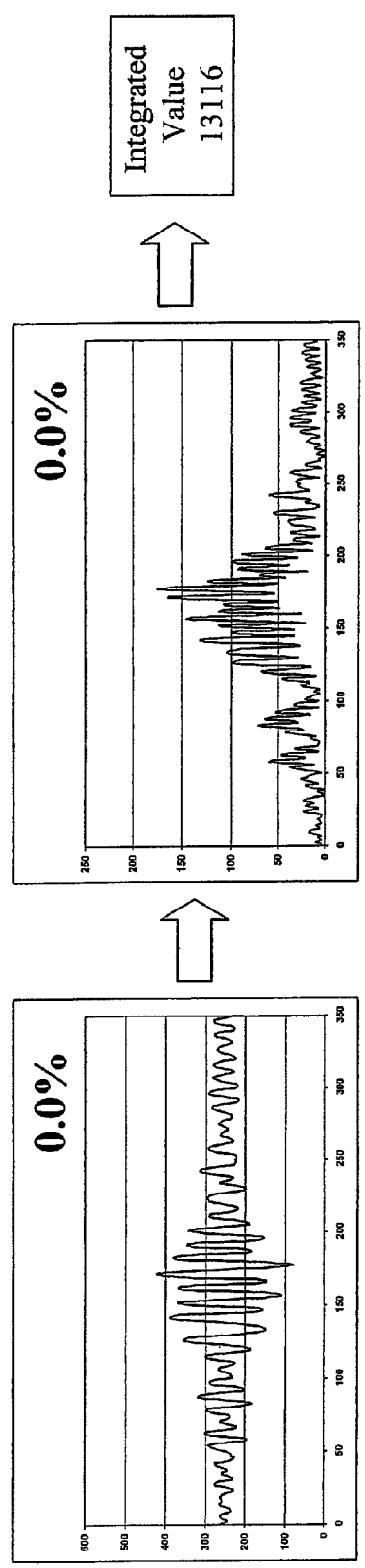

FIG. 4A graphically represents the signals received by an ultrasonic receiver during the inspection of a workpiece with little porosity, few microcracks and little heat damage in accordance with one embodiment of the present invention;

FIG. 4B graphically represents the signals received by an ultrasonic receiver during the inspection of a workpiece with more substantial porosity, more microcracks and/or more substantial heat damage in accordance with one embodiment of the present invention;

FIG. 5 graphically depicts the digitization, rectification and summation of the signals received by an ultrasonic receiver during the inspection of a workpiece with more substantial porosity, more microcracks and/or more substantial heat damage in accordance with one embodiment of the present invention; and FIG. 6 graphically depicts the digitization, rectification and summation of the signals received by an ultrasonic receiver during the inspection of a workpiece with little porosity, few microcracks and little heat damage in accordance with one embodiment of the present invention.

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Figure 1:
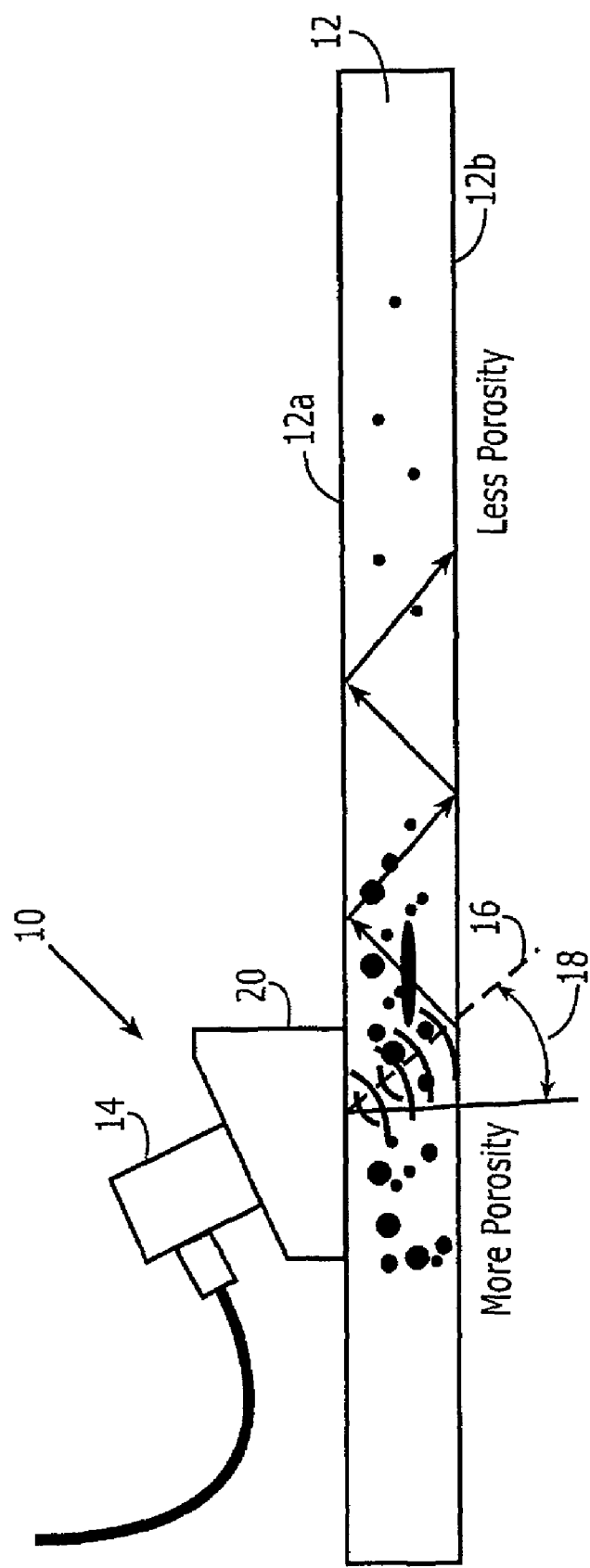
FIG. 1 is a schematic representation of the orientation of the ultrasonic transmitter and ultrasonic receiver relative to a workpiece in accordance with one embodiment of the present invention.

Referring now to FIG. 1, a portion of an apparatus 10 for ultrasonically inspecting a workpiece 12, such as for porosity, microcracking or for thermal damage, is depicted. The ultrasonic inspection apparatus can inspect a variety of structures formed of various materials. Structures that may be inspected with an embodiment of an inspection apparatus may include, but are not limited to, composites such as carbon fiber or graphite reinforced epoxy (Gr/Ep) composites or foam filled composites, non-ferromagnetic metals (e.g. aluminum alloy, titanium alloy, or aluminum or titanium hybrid laminates such as GLARE or Ti/Gr), ferromagnetic metals, plastics, ceramics, polymers and virtually all solids, semi-solids and even liquids. While a portion of a relatively simple structure is depicted in FIG. 1, a structure being inspected may be any myriad of shapes and/or sizes and used in a variety of applications, including aircraft, marine vehicles, automobiles, spacecraft and the like, as well as buildings. For example, the structure may be a foam filled hat stiffener or hat stringer. Moreover, the structure may be inspected prior to assembly, such as for porosity, or following assembly, such as for microcracking and/or thermal damage, as described below.

The ultrasonic inspection apparatus 10 is generally configured for single-sided inspection of the workpiece 12 as a result of its reliance upon backscattered signals. As such, the ultrasonic inspection apparatus is operable to inspect structures in instances in which the opposite side 12b of the structure is inaccessible. For example, the ultrasonic inspection apparatus is operable to inspect structures during manufacture in instances in which the structure is supported upon a mandrel or other tooling with the opposite or back side of the structure facing the mandrel or other tooling. Similarly, the ultrasonic inspection apparatus is operable to inspect structures following deployment even if only a single side 12a is accessible, thereby potentially reducing instances in which the structure must be disassembled and/or removed from the field for inspection.

The ultrasonic inspection apparatus 10 includes an ultrasonic transmitter that includes one or more ultrasonic transducers 14 oriented in such a manner as to introduce ultrasonic signals that propagate along an axis 16 positioned at an offset angle 18 relative to a predefined reference direction oriented normal to the surface 12a of the structure that faces the inspection apparatus. The offset angle may have various predefined values, but is typically an acute, non-zero angle, such as between 5° and 45° and, in one embodiment, between 5° and 15° relative to the predefined reference direction. The ultrasonic transmitter may emit ultrasonic signals at any of a plurality of different frequencies. Typically, the frequency of the ultrasonic signals varies in an inverse relationship to the thickness of the workpiece to be inspected. For example, the ultrasonic transmitter may transmit signals having a frequency of 10 MHZ for the inspection of thinner structures and a frequency of either 2.25 MHZ or 3.5 MHZ for the inspection of thicker structures. In one embodiment, however, the ultrasonic transmitter emits signals having a frequency of 5 MHZ.

In one embodiment, the ultrasonic transducer 14 is carried by wedge or shoe 20 that defines the offset angle 18. The shoe may be formed of various materials, such as materials transparent to ultrasonic signals including, for example, acrylic. The ultrasonic transducer may be carried by the shoe in different manners including, for example, a transducer mount for supporting, engaging and orienting the transducer. For example, a threaded ring may be mounted to the shoe, such as by a number of screws, and the transducer may be threadably connected to the ring. Alternatively, a slip ring may be placed into a groove that is machined into the body of the transducer and the transducer may then be slid into a horizontal gap defined by the shoe. Depending upon the application and inspection environment, a couplant, such as an ultrasonic gel or water, may be applied between the shoe and the surface 12a of the structure 12 to provide a good path from the transducer into the structure, and possibly as a lubricant for moving the probe over the surface of the structure. Additionally, couplant may be applied between the tranducer and the shoe. The shoe may include contact members to support the shoe against the respective surface of the structure. A contact member may be any variety of devices capable of supporting the shoe against a surface of a part, including, but not limited to, a wheel, a ball bearing, a fluid bearing, a skid, a tread, or a combination of the aforementioned contact members.

The ultrasonic inspection apparatus 10 may also include an encoder to record the position of the ultrasonic transducer 14 relative to the workpiece 12 so as to permit the resulting backscattered signals discussed below to be associated with a respective position. Various types of encoders may be employed including, for example, a positional encoder, an optical encoder, a linear encoder, a camera, a directional sensor, or a wheel encoder.

Although the transducer(s) 14 and the shoe 20 may be moved manually over the surface 12a of the workpiece 12, the transducers(s) and the shoe may be moved over the surface of the workpiece, such as in a predefined pattern, in an automated or semi-automated fashion. For example, the inspection apparatus 10 may include a motor, such as an electronically-controlled stepper motor, that is operably connected to the transducer(s) and the wedge for controllably moving the transducer(s) and the shoe across the surface of the structure.

Figure 2:
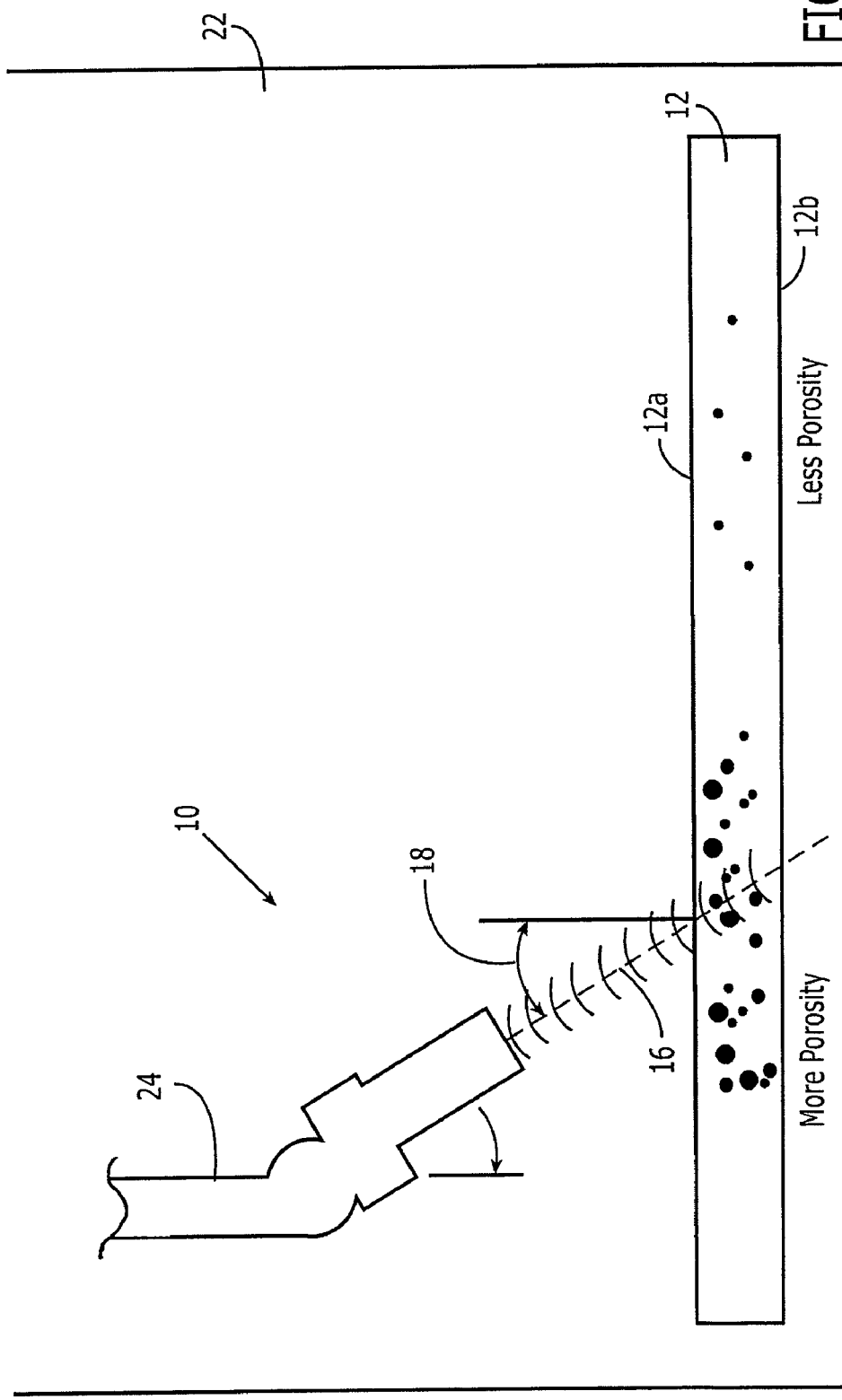
FIG. 2 is a schematic representation of the orientation of the ultrasonic transmitter and ultrasonic receiver relative to a workpiece in accordance with another embodiment of the present invention which employs a robotic scanner.

In an alternative embodiment designed to operate in an immersion mode and depicted in FIG. 2, the inspection apparatus 10 may include an immersion tank 22 containing a couplant, such as water. The transducer(s) may be carried by an arm 24 attached to a robotic scanner, such as the UPKII-T48HD C-Scan system with 3 (x-y-z) motion axis and linear actuator drive, manufactured by NDT Automation. The transducer(s) may also be in a phased array format, with an array that is moved along with a robotic arm or manually, such as an Omniscan scanner distributed by Olympus NDT, Inc. Phased array systems allow steering of the ultrasonic beam so an angled beam can be produced without an angled wedge for a transducer shoe. Phased array systems could be mounted at an angle for immersion tests as described below or mounted on wedges or shoes for other types of tests. In an immersion test, the transducer(s) are immersed within the tank so as to be disposed at the desired offset angle relative to the normal to the surface of the structure. The robotic scanner may then be configured to move the transducer(s) in a predefined path through the tank so as to interrogate the structure along the predefined path. In order to associate the backscattered signals with respective locations upon the workpiece, the robotic scanner can be configured to initially place the transducer(s) 14 at a predefined location relative to the workpiece and to then track the motion of the transducer(s) relative to the workpiece.

Still further, the transducer(s) could be mounted into a dribbler and, using a floating z-axis, can be utilized to inspect a workpiece essentially using an immersion technique. In this embodiment, a dribbler includes a transducer mounted inside an enclosure with water or other couplant pumped into the enclosure at a rate such that the water or other couplant dribbles out of the bottom of the enclosure so as to provide both a path for the signal and a couplant for the workpiece.

Figure 3:
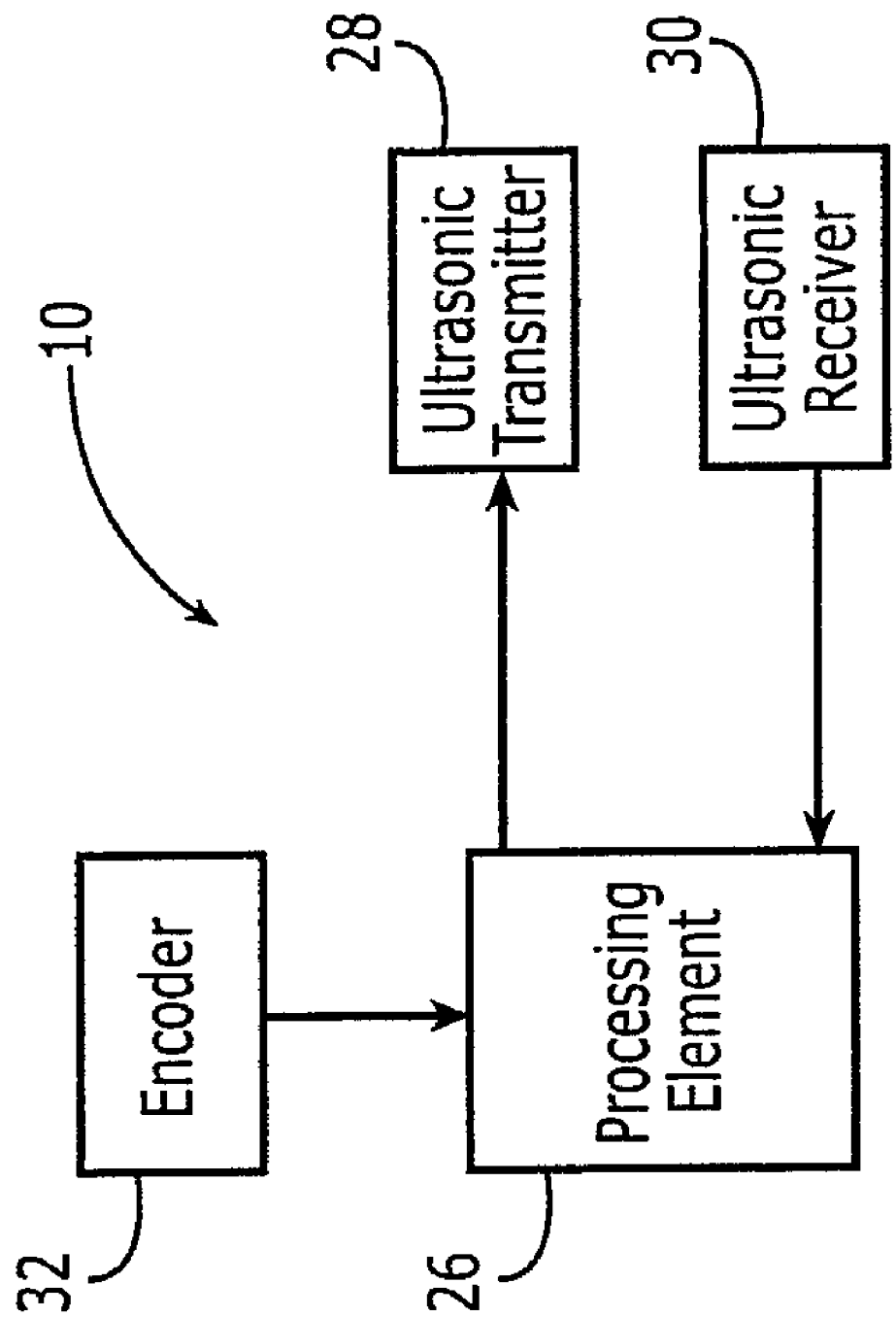
FIG. 3 is a block diagram of an apparatus according to one embodiment of the present invention.

As shown in FIG. 3, the inspection apparatus 10 also generally includes a processing element 26, such as a personal computer, a microcontroller, a microprocessor, an application specific integrated circuit (ASIC) or other type of computing device, that serves as a control apparatus for controlling movement of the ultrasonic transmitter 28, e.g., the transducer(s) 14, is scanned in automated or semi-automated embodiments, such as those utilizing a motor or a robot, and for actuating the ultrasonic transmitter in order to generate the ultrasonic signals. The inspection apparatus also includes an ultrasonic receiver 30 for receiving the ultrasonic signals that are backscattered by the workpiece 12, such as by the porosity, by microcracks or by the thermal damage as described below. In one embodiment, the inspection apparatus includes ultrasonic transducer(s) that function as both the ultrasonic transmitters and the ultrasonic receivers. In order to associate the backscattered signals with a respective location upon the workpiece, the processing element of one embodiment is also configured to receive signals indicative of the position of the transducer(s), such as from an encoder 32 as shown in FIG. 3, a robotic scanner of the like.

In operation, the inspection apparatus 10 is positioned relative to the workpiece 12, such as shown in FIGS. 1 and 2, at a predefined location. The processing element 26 then actuates the ultrasonic transmitter, such as an ultrasonic transducer 14, to transmit an ultrasonic signal into the workpiece. Although the processing element can actuate the ultrasonic transmitter 28 and in turn, the ultrasonic receiver 30 in various manners, the processing element of one embodiment includes an ultrasonic pulser receiver module or card for actuating the ultrasonic transmitter and receiver. As described, the ultrasonic signals transmitted by the transducer propagate along an axis 16 that is disposed at an offset angle 18 from a normal to the surface 12a of the workpiece. Upon encountering defects, such as porosity, a microcrack or thermal damage, a portion of the ultrasonic signals are backscattered as shown by the arcuate lines of FIG. 1, and at least a portion of the backscattered signals are received and detected by the ultrasonic receiver. A large defect, such as a delamination, a disbond or the like, will not tend to scatter the signals, but will reflect the signals away from the transducer because of the angle. The backscattered signals attributable to the interaction of the ultrasonic signals with any single pore, microcrack or any single void or other defect created by thermal damage is relatively small, but measurable. In order to evaluate the porosity, microcracking or the thermal damage of the workpiece at the respective location, the sum of the backscattered signals attributable to a plurality of the pores, a plurality of microcracks or a plurality of the defects attributable to thermal damage at the respective locations, such as all of the pores, microcracks or all of the defects attributable to the thermal damage in the beam path, is determined, since it is only in the aggregate that the effects of porosity or microcracking or of the defects attributable to thermal damage upon the structure in that location can generally be assessed.

In this regard, the processing element 26 generally receives the output from the ultrasonic receiver 30, e.g., one or more transducer(s) 14, over a predefined period of time with the output of the ultrasonic receiver being representative of the amplitude of the signals received by the ultrasonic receiver over the predetermined period of time. In one embodiment, the processing element includes a digitizer for converting analog signals provided by the ultrasonic receiver to corresponding digital signals. Additionally, the processing element can include a rectifier for rectifying the signals produced by the ultrasonic receiver either prior to or following analog-to-digital conversion. As shown in FIG. 4A, the digitized and rectified signals representative of the amplitude of the backscattered signals received by the ultrasonic receiver are smaller when a structure having little porosity, few microcracks and little heat damage is suspected. Alternatively, the digitized and rectified signals representative of the amplitude of the backscattered signals received by the ultrasonic receiver are larger over time when the structure has more substantial porosity, more microcracks or has suffered heat damage as shown in FIG. 4B. In some embodiments, the processing element may also adjust the signals received from the ultrasonic receiver to remove any contribution, e.g., attenuation, created by the shoe 20.

By integrating or summing the signals, e.g., once digitized and rectified, representative of the amplitude of the backscattered signals received by the ultrasonic receiver 30 over a predetermined period of time, the processing element 26 can determine a measure representative of the degree of porosity, microcracking or thermal damage of the workpiece 12 at the respective location. The processing element can then compare the sum of the backscattered signals received by the ultrasonic receiver with a predefined threshold, and the processing element can provide an indication of whether the workpiece at the respective location has an unacceptable degree of porosity, an unacceptable amount of microcracking or an unacceptable amount of thermal damage based upon the relationship of the sum of the backscattered signals received by the ultrasonic receiver to the predefined threshold. Typically, the predefined threshold is set to a value such that the sum of the backscattered signals received by the ultrasonic receiver over the predefined period at any location is indicative of an unacceptable level of porosity, microcracking or thermal damage if the sum exceeds a predefined threshold. Conversely, if the sum of the backscattered signals received by the ultrasonic receiver is less than the predefined threshold, the workpiece will generally be found to have acceptable levels of porosity, microcracking and thermal damage at the respective location. The value of the predefined threshold may vary, depending upon the application, the loads that are anticipated to be placed upon the workpiece and the tolerance of the workpiece and/or the application to the structural degradation occasioned by porosity, microcracking or thermal damage, among other factors.

Although the predefined threshold may be defined in various manners, the predefined threshold may be determined by inspecting several samples constructed of the same materials and in the same thickness and configuration as the workpiece 12, but having different known levels of porosity, microcracking and/or thermal damage—some of which being known to be acceptable and others of which being known to be unacceptable. By comparing the measure representative of the degree of porosity, microcracking or thermal damage for each of the samples and determining those measures that are reflective of acceptable samples and those reflective of unacceptable samples, the threshold representative of the dividing line between acceptable and unacceptable levels of porosity, microcracking or thermal damage may be predefined.

The predetermined time period over which the backscattered signals received by the ultrasonic receiver 30 are summed generally corresponds to the thickness of the workpiece 12 or, at least, the thickness of the portion of the workpiece that is desirably inspected. In this regard, the predetermined time period is generally set to equal or slightly exceed the time required for ultrasonic signals to propagate through the workpiece or at least that portion of the workpiece that is desired to be inspected and to then return to the ultrasonic receiver. While the predetermined time period can have a wide range of values depending upon the thickness of the workpiece or at least the thickness of that portion of the workpiece that is desirably inspected, the predetermined time period is typically one to a few microseconds.

By way of example, the leftmost graphs in FIGS. 5 and 6 illustrate the digitized output of an ultrasonic receiver 30 in terms of the relative ultrasonic amplitude of the backscattered signals over a period of 350 microseconds during the inspection of structures having a porosity of 6.15% and 0%, respectively. The relative ultrasonic amplitude of the backscattered signals represent the voltage produced by the piezoelectric transducer of the ultrasonic receiver as the ultrasonic (stress) waves impinge upon the face of the transducer. The relative ultrasonic amplitude is typically measured in digitizer units with the actual voltage being unimportant so long as no changes are made to the ultrasonic transmitter and receiver during a test. In turn, the rightmost graphs of FIGS. 5 and 6 depict the same output following rectification. By integrating the area under the respective graphs, a measure of 39,043 is obtained for the structure having a porosity of 6.15% and a measure of 13,116 is obtained for the structure having a porosity of 0%. As such, FIGS. 5 and 6 graphically illustrate the relationship between the area under the curve and the porosity (or likewise, microcracking or thermal damage) of a structure.

While the summation of the amplitudes of the backscattered signals received by the ultrasonic receiver 30 over a predetermined period of time permits the aggregate effect of pores, microcracks or defects attributable to thermal damage to be determined in instances in which the effect of a single pore (or a small number of pores), a single microcrack (or a small number of microcracks) or a single defect (or a small number of defects) attributable to thermal damage would otherwise be insignificant, the propagation of the ultrasonic signals at an offset angle relative to the normal to the surface of the workpiece also advantageously permits the ultrasonic inspection apparatus to obtain reliable results indicative of the porosity, microcracking or thermal damage of the workpiece. In this regard, reflections from the front surface 12a or back surface 12b of the workpiece or from larger delaminations or disbonds within the workpiece cause a portion of the ultrasonic signals to be reflected. As a result of the propagation of the ultrasonic signals at the offset angle relative to the normal to the surface of the workpiece, the reflections of the ultrasonic signals do not return to the transducer, but are reflected at an angle based upon Snell's Law as schematically represented by FIGS. 1 and 2. By avoiding the reflection of the ultrasonic signals from the front and back surfaces of the workpiece or from delaminations or disbonds from being detected by the ultrasonic receiver, the backscattered signals received by the ultrasonic receiver are not washed out or otherwise rendered insignificant as a result of the receipt of reflected signals having a larger, sometimes much larger, amplitude.

In operation, the ultrasonic inspection apparatus 10 and, in particular, the ultrasonic transmitter 28 initially transmits ultrasonic signals into the workpiece 12 at an initial location and the ultrasonic receiver 30 receives backscattered signals over a predetermined period of time. Following the predetermined period of time, the ultrasonic transmitter and receiver, e.g., the ultrasonic transducer(s) 14 and shoe 20, may be moved along the surface 12a of the workpiece to a second position and the process of injecting ultrasonic signals and receiving the backscattered signals over a predetermined period of time can be repeated. This iterative process can be repeated any number of times as the ultrasonic transmitter and receiver, e.g., the ultrasonic transducer(s), are moved, typically in a predefined pattern, along the surface of the workpiece.

The results of the inspection can be processed in many different manners. For example, the sum of the amplitude of the backscattered signals within a predefined period of time at each respective location can be stored and then analyzed to identify location(s) which would appear to have an undesirable amount of porosity, microcracking or thermal damage. In this regard, the inspection apparatus 10 can transmit the data, such as in either a wireline or wireless manner, to another computing device for subsequent analysis, such as to identify location(s) which would appear to have an undesirable amount of porosity, microcracking or thermal damage. Alternatively, the processing element 26 of the ultrasonic inspection apparatus can compare the sum of the amplitude of the backscattered signals received by the ultrasonic receiver 30 over a predetermined period of time at each location and provide a warning, an alarm or the like to the operator of the inspection apparatus during the course of the inspection of any location(s) that appear to have an unacceptable degree of porosity, microcracking or thermal damage. Moreover, the results can be presented in a variety of manners, including in a numerical format representative of the sum of the amplitudes of the backscattered signals over a predetermined period of time at the different locations or graphically in which the sums of the amplitudes of the backscattered signals at each location are graphically depicted.

As noted above, the ultrasonic inspection apparatus 10 can be deployed for various applications, including the inspection of a workpiece 12 during manufacture, in which case the ultrasonic inspection apparatus would generally inspect the workpiece for porosity, or following placement of the workpiece into service in the field, in which instances the ultrasonic inspection apparatus would generally inspect the workpiece for the effects of microcracking or thermal damage. Advantageously, the ultrasonic inspection apparatus is generally capable of injecting the ultrasonic signals into the workpiece and receiving the backscattered signals from the workpiece, even in instances in which the surface of the workpiece that faces the ultrasonic inspection apparatus has been primed, painted or includes lightening strike protection. Ultrasonic inspection can be performed of structures that have been primed, painted or include lightening strike protection because these features will only slightly attenuate the ultrasonic signal. If a feature, such as paint, is thin compared to the wavelength of the ultrasound signals and/or the impedance mismatch at the boundaries is small, the ultrasound signals will tend to penetrate through the feature. A large impedance mismatch, such as between a material and air, will cause a very strong reflection at the boundary, and only a small percentage of the ultrasonic signal will penetrate the material. This larger impedance mismatch is what leads to the general use of a coupant between the transducer 14 and the workpiece 12. In contrast, thin coatings produce a strong reflection at the interface with the structure (thus obscuring that structure) only at very high frequencies where the wavelengths are very small. As such, the inspection apparatus of embodiments of the present invention is particularly suitable for inspecting workpieces in the field following the application of primer, paint and/or lightening strike protection.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A method of inspecting a workpiece comprising:
   introducing ultrasonic signals into the workpiece along a predefined axis of propagation oriented at an offset angle relative to a predefined reference direction oriented normal to the workpiece;
   receiving back scattered signals from the workpiece responsive to the ultrasonic signals;
   determining a measure representative of the cumulative energy of the backscattered signals received over a predefined time interval by integrating the energy of the backscattered signals received over the predefined time interval, wherein the predefined time interval is based upon and at least as long as the time required for ultrasonic signals to propagate through at least that portion of the workpiece that is to be inspected; and detecting an anomalous response from the workpiece based upon the measure representative of the cumulative energy of the backscattered signals.

2. A method according to claim 1 wherein introducing the ultrasonic signals comprises introducing the ultrasonic signals at an offset angle of between 5° and 45° relative to the predefined reference direction.

3. A method according to claim 1 wherein detecting an anomalous response comprises detecting an anomalous response representative of at least a predefined amount of porosity within the workpiece.

4. A method according to claim 1 wherein detecting an anomalous response comprises detecting an anomalous response representative of thermal damage to the workpiece.

5. A method according to claim 1 wherein detecting an anomalous response comprises detecting an anomalous response representative of at least a predefined amount of microcracking within the workpiece.

6. A method according to claim 1 wherein introducing ultrasonic signals into the workpiece and receiving ultrasonic signals from the workpiece are repeated at a plurality of locations across the workpiece.

7. An inspection apparatus comprising:

an ultrasonic transmitter configured to introduce ultrasonic signals into the workpiece along a predefined axis of propagation oriented at an offset angle relative to a predefined reference direction oriented normal to the workpiece;

an ultrasonic receiver configured to receive back scattered signals from the workpiece responsive to the ultrasonic signals; and a processing element configured to determine a measure representative of the cumulative energy of the backscattered signals received over a predefined time interval and to detect an anomalous response from the workpiece based upon the measure representative of the cumulative energy of the backscattered signals, wherein determining a measure representative of the cumulative energy of the backscattered signals comprises integrating the energy of the backscattered signals received over the predefined time interval, and wherein the predefined time interval is based upon and at least as long as the time required for ultrasonic signals to propagate through at least that portion of the workpiece that is to be inspected.

8. An inspection apparatus according to claim 7 wherein said ultrasonic transmitter is configured to introduce the ultrasonic signals at an offset angle of between 5° and 45° relative to the predefined reference direction.

9. An inspection apparatus according to claim 7 wherein said processing element is configured to detect an anomalous response representative of at least a predefined amount of porosity within the workpiece.

10. An inspection apparatus according to claim 7 wherein said processing element is configured to detect an anomalous response representative of thermal damage to the workpiece.

11. An inspection apparatus according to claim 7 wherein said processing element is configured to detect an anomalous response representative of at least a predefined amount of microcracking within the workpiece.

12. An inspection apparatus according to claim 7 further comprising a shoe defining the offset angle and carrying at least a portion of the ultrasonic transmitter.

13. An inspection apparatus according to claim 12 wherein the ultrasonic transmitter carried by the shoe comprises at least one ultrasonic transducer, and wherein the shoe comprises an angled shoe.

14. An inspection apparatus according to claim 12 wherein the ultrasonic transmitter carried by the shoe comprises a phased array of ultrasonic transducers.

15. A control apparatus comprising:

a processing element configured to direct an ultrasonic transmitter to introduce ultrasonic signals into the workpiece along a predefined axis of propagation oriented at an offset angle relative to a predefined reference direction oriented normal to the workpiece, said processing element also configured to direct an ultrasonic receiver to receive back scattered signals from the workpiece responsive to the ultrasonic signals, said processing element further configured to determine a measure representative of the cumulative energy of the backscattered signals received over a predefined time interval and to detect an anomalous response from the workpiece based upon the measure representative of the cumulative energy of the backscattered signals, wherein the processor is configured to determine a measure representative of the cumulative energy of the backscattered signals by integrating the energy of the backscattered signals received over the predefined time interval, and wherein the predefined time interval is based upon and at least as long as the time required for ultrasonic signals to propagate through at least that portion of the workpiece that is to be inspected.

16. A control apparatus according to claim 15 wherein said processing element is configured to detect an anomalous response representative of at least a predefined amount of porosity within the workpiece.

17. A control apparatus according to claim 15 wherein said processing element is configured to detect an anomalous response representative of thermal damage to the workpiece.

18. A control apparatus according to claim 15 wherein said processing element is configured to detect an anomalous response representative of at least a predefined amount of microcracking within the workpiece.

* * * * *